United States Patent [19]

Schwartz

[11] Patent Number: 4,618,935
[45] Date of Patent: Oct. 21, 1986

[54] LIQUID CHROMATOGRAPHY CONTROLLER

[75] Inventor: Arnold Schwartz, Bridgeport, Conn.
[73] Assignee: The Perkin-Elmer Corporation, Norwalk, Conn.
[21] Appl. No.: 568,765
[22] Filed: Jan. 6, 1984
[51] Int. Cl.[4] .................... G06G 7/57; G01N 31/00
[52] U.S. Cl. .................... 364/510; 73/61.1 C; 364/497
[58] Field of Search ............ 364/497, 500, 502, 509, 364/510; 73/23.1, 61.1 C, 203, 863.21; 23/306; 210/198 C

[56] References Cited

U.S. PATENT DOCUMENTS

| | | | |
|---|---|---|---|
| 3,965,341 | 6/1976 | Honey et al. | 364/510 |
| 4,063,077 | 12/1977 | Wright | 364/497 X |
| 4,066,879 | 1/1978 | Leaver et al. | 73/61.1 C |
| 4,084,246 | 4/1978 | Schwartz | 364/510 |
| 4,191,649 | 3/1980 | Hartwick | 73/61.1 C |
| 4,220,998 | 9/1980 | Kays | 364/510 |
| 4,233,156 | 11/1980 | Tsukada et al. | 73/61.1 C |
| 4,237,422 | 12/1980 | Lenhardt | 73/23.1 |
| 4,254,460 | 3/1981 | Achter et al. | 364/497 |

Primary Examiner—Errol A. Krass
Assistant Examiner—Kevin J. Teska
Attorney, Agent, or Firm—E. T. Grimes; F. L. Masselle

[57] ABSTRACT

A new and improved controller for creating a linear gradient dual solvent flow pattern in a dual pump liquid chromatography system wherein one pump pumps one solvent and the other pump pumps the second solvent, the controller comprising a clock for producing a timing signal; digiswitches for providing first and second digital signals representative of initial and final values for one of two solvents; a difference circuit for producing a third digital signal representative of the difference between the initial and final values; a digiswitch for providing a fourth digital signal representative of the time duration of the linear gradient; a binary divider for regulating the timing signal to produce a signal proportional to the fourth digital signal; a binary rate multiplier for proportioning the regulated timing signal to the third digital signal; circuitry for producing a fifth digital signal from the proportional regulated timing signal, whereby the fifth digital signal represents the dividend of the third digital signal divided by the fourth digital signal; and circuitry for inputting signals to each of the pumps to set the flow rates thereof, said circuitry being regulated by said fifth digital signal.

11 Claims, 8 Drawing Figures

LIQUID CHROMATOGRAPHY CONTROLLER

FIELD OF INVENTION

This invention relates to Liquid Chromatography Systems and, more particularly, to a controller for creating a linear gradient dual solvent flow pattern in a dual pump liquid chromatography system.

BACKGROUND OF THE INVENTION

In the field of Liquid Chromatography, an unknown substance is introduced along with a solvent solution into a column. The solvent solution is usually comprised of one or more liquids which are mixed together in known proportions. However, during testing of a particular sample, it has been found desirable to change the proportions of the individual liquids which comprise the solvent solution into which the sample is introduced. As a result, solvent gradients are useful, inter alia, for optimizing separation time or for choosing an isocratic composition for an unfamiliar separation. Generally, if an isocratic separation can be performed in a reasonable time period, there is no need to implement a gradient. However, if a separation involves extensive time, such as for example 30 minutes, the use of a gradient may be useful. If the earliest peaks of a chromatogram are unresolved and the later peaks are eluted slowly, either a gradient or a different column/mobile phase combination is necessary.

In many instances, liquid chromatography systems are designed to accommodate only a single solvent, i.e. to perform isocratic separations. However, two such systems can be coupled, via a control mechanism to perform linear solvent gradient analysis. Heretofore, conventional control mechanism relied upon either analog circuits. As a result, the accuracy of such conventional control mechanisms was susceptible to temperature changes and signal drift. Hence, the output signal to the pumps, being controlled, varied and was frequently difficult to reproduce.

A related reference in this field is U.S. Pat. No. 4,084,246 issued Apr. 11, 1978, which is directed to a generator for controlling the flow rate of two solvents where it is desired to maintain the total flow of the two solvents constant while permitting precise control of the percent of one solvent in the mixture.

While the above prior art systems have met with success for their intended purposes, the present invention is directed to improvements thereover, particularly with respect to certain installations, as will become apparent as the description proceeds.

SUMMARY OF THE INVENTION

Accordingly, it is one object of the present invention to provide a new and improved controller for creating a linear gradient dual solvent flow pattern in a dual pump liquid chromatography system, which is substantially free of errors due to drift, which produces reproducible output signals, and which allows the gradient duration to be selected and automatically determines the rate from the other inputted parameters.

This object is accomplished, at least in part, by a controller which is characterized by a plurality of discrete digital elements. In order to accomplish the desired results, the present invention provides, in one form thereof, a new and improved controller which includes clock means for producing a timing signal, means for providing first and second digital signals representative of initial and final values for one of the two solvents, means for producing a third digital signal representative of the difference between the initial and final values. In addition the controller employs means for providing a fourth digital signal representative of the time duration of the linear gradient, digital means for regulating the timing signal to produce a signal proportional to the fourth digital signal, and means for proportioning the regulated timing signal to the third digital signal. In addition, the combination includes means for producing a fifth digital signal from said proportional regulated timing signal, whereby the fifth digital signal represents the dividend of the third digital signal divided by the fourth digital signal, and means for inputting signals to each of the pumps to set the flow rate thereof, said last named means being regulated by the fifth digital signal.

There has thus been outlined rather broadly the more important features of the invention in order that the detailed description thereof that follows may be better understood, and in order that the present contribution to the art may be better appreciated. There are, of course, additional features of the invention which will be described more fully hereinafter. Those skilled in the art will appreciate that the conception on which this disclosure is based may readily be utilized as the basis for the designing of other devices for carrying out the several purposes of the invention. It is important, therefore, that this disclosure be regarded as including such equivalent devices as do not depart from the spirit and scope of the invention.

One embodiment of the invention has been chosen for purposes of illustration and description, and is shown in the accompanying drawings, forming a part of the specification.

BRIEF DESCRIPTION OF THE DRAWINGS

FIG. 4 shows how FIGS. 4A, 4B and 4C comprise a circuit diagram of one actual implementation of the invention.

DETAILED DESCRIPTION OF A PRESENTLY PREFERRED EMBODIMENT

Figure 1:
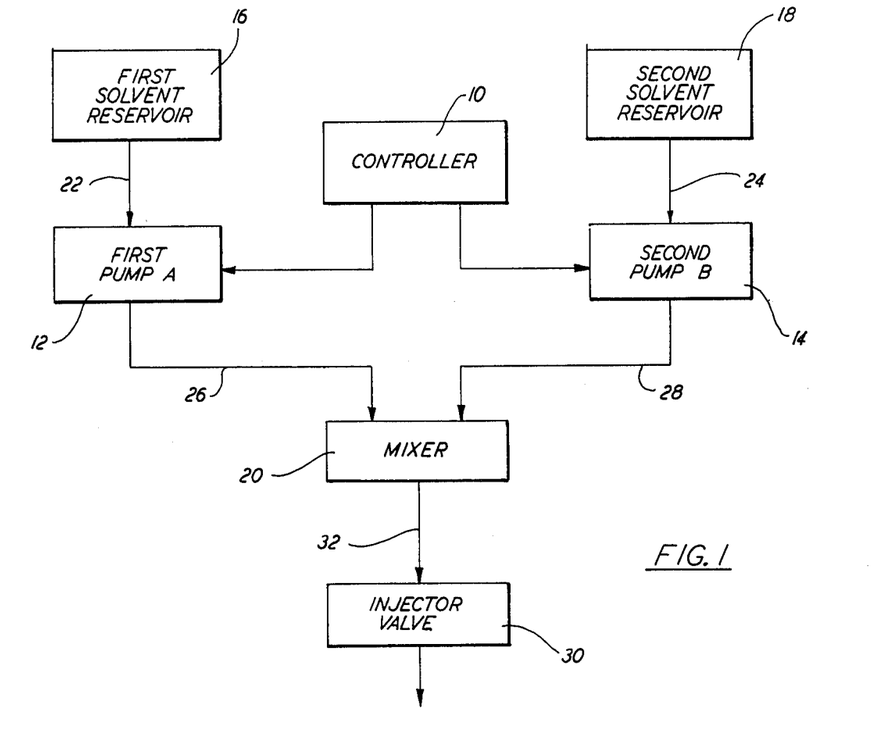
FIG. 1 is a block diagram of the pump configuration of a liquid chromatography system utilizing a digital control circuit embodying the principles of the present invention.

With reference to FIG. 1, a liquid chromatography system is illustrated which includes a controller 10, first pump (A) 12 and second pump (B) 14, first and second solvent reservoirs 16 and 18, respectively, and a mixer 20. The reservoirs, 16 and 18 are connected to the pumps, 12 and 14, by pump inlet conduits, 22 and 24, respectively. The first and second pumps, 12 and 14 are connected to the mixer 20 via pump outlet conduits, 26 and 28, respectively. The mixer 20 is coupled in fluid flow relationship to an injector valve 30 via conduit 32, provided for the purpose. The pumps 12, 14 are controlled by the controller 10, as will be described more fully hereinafter.

The purpose of the system of FIG. 1 is to deliver the proper proportions of the solvents from the reservoirs 16 and 18. The percent of the total volume of one of the solvents is linearly increased while the percent of the total volume of the other solvent is linearly decreased, whereby the total volume remains constant. According to the invention, this gradient is controlled so that it takes place within a preselected time period. This feature is particularly advantageous because the peak distribution, i.e. the time duration of a separation, on a chromatogram is critical to the chromatography of the sample.

Figure 2:
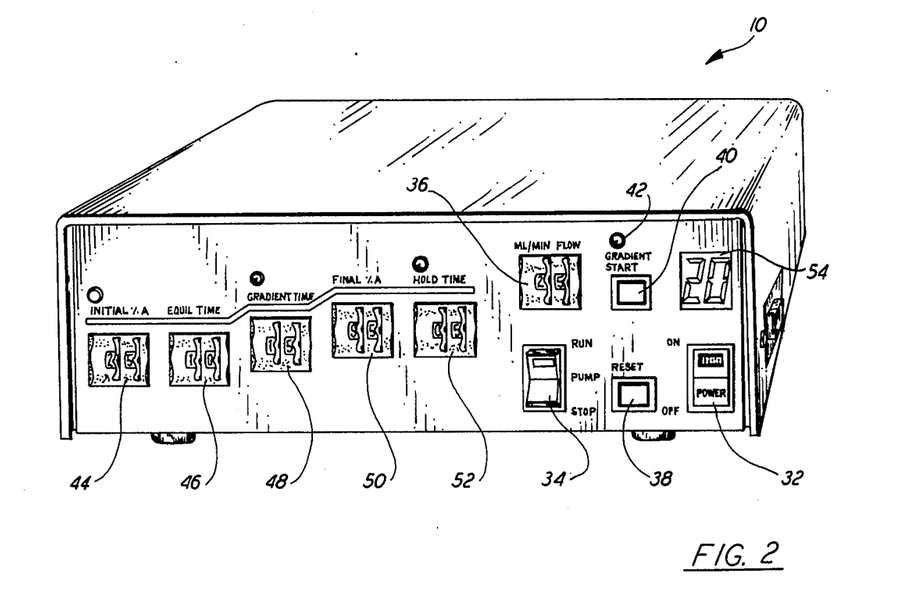
FIG. 2 is a perspective view of a controller for use in the system of FIG. 1.

Referring next to FIG. 2, there is depicted the controller 10 of FIG. 1. Paddle handle switch 32 controls the application of power to the controller. A rocker switch 34 is used to apply the drive signals from the controller 10 to the pumps 12, 14. It is spring loaded to a neutral position. A flow rate digiswitch 36 allows the flow rate to be changed, such as for example, from 0.0 to 9.9 ml/min. The flow rate may be changed at any time. A momentary reset push button switch 38 is used to "load" any digiswitch setting, other than FLOW, into the controller. Depression of the reset switch also sets the % A LED display to initial value. A Gradient Start push button switch 40 starts a gradient program when depressed. The Gradient Start switch only functions after the controller has come to a ready condition. This is indicated by a red light emitting diode (LED) 42 directly above the switch.

A digiswitch called Initial % A indicated at 44, FIG. 2, is employed to set the starting composition of the mobile phase. The composition will remain at this value until the controller is given a command to start a gradient. This switch is setable from 00 to 99, however, the useful range for chromatography is normally from about 10 to about 90. An Equil Time digiswitch 46 allows the operator to set a minimum time for system equilibration. A gradient can not be started until this time has elapsed. After the expiration of the Equil Time, the composition will remain at the Initial % A setting until the controller has received a command to start a gradient. The switch is both settable and useable from 00 minutes to 99 minutes. A Gradient Time digiswitch 48 is settable for gradient durations of from 00 to 99 minutes using the controller. A digiswitch called Final % A, indicated at 50, is used to set the ending composition of the mobile phase. The composition will remain at this value until the controller is given a command to reset back to Initial % A. The switch is settable from 00 to 99. The normal useful range for chromatography is from about 10 to about 90. A Hold Time digiswitch 52 serves to set the amount of time that the controller will remain at the Final % A setting. This is useful to insure that strongly retained components will be eluted from the column. The controller will remain at the Final % A setting for this entire period of time unless it receives a reset command. The switch is both settable and useful from 00 to 99 minutes. A two digit LED display 54 always reads the percentage of solvent A that the mobile phase contains. It is noted that the controller will not recognize a change in the Initial % A Equil Time, Gradient Time, Final % A, and Hold Time digiswitches until a reset command is given or until the Hold Time has elapsed. Whenever the Initial % A and Final % A values are the same, the controller will automatically advance into Hold Time at the expiration of Equal Time. These percent A values must be the values the controller recognizes. If they were not the same and then changed, the Reset push button must be depressed before the controller recognizes them as being equal.

Figures 3, 3A:
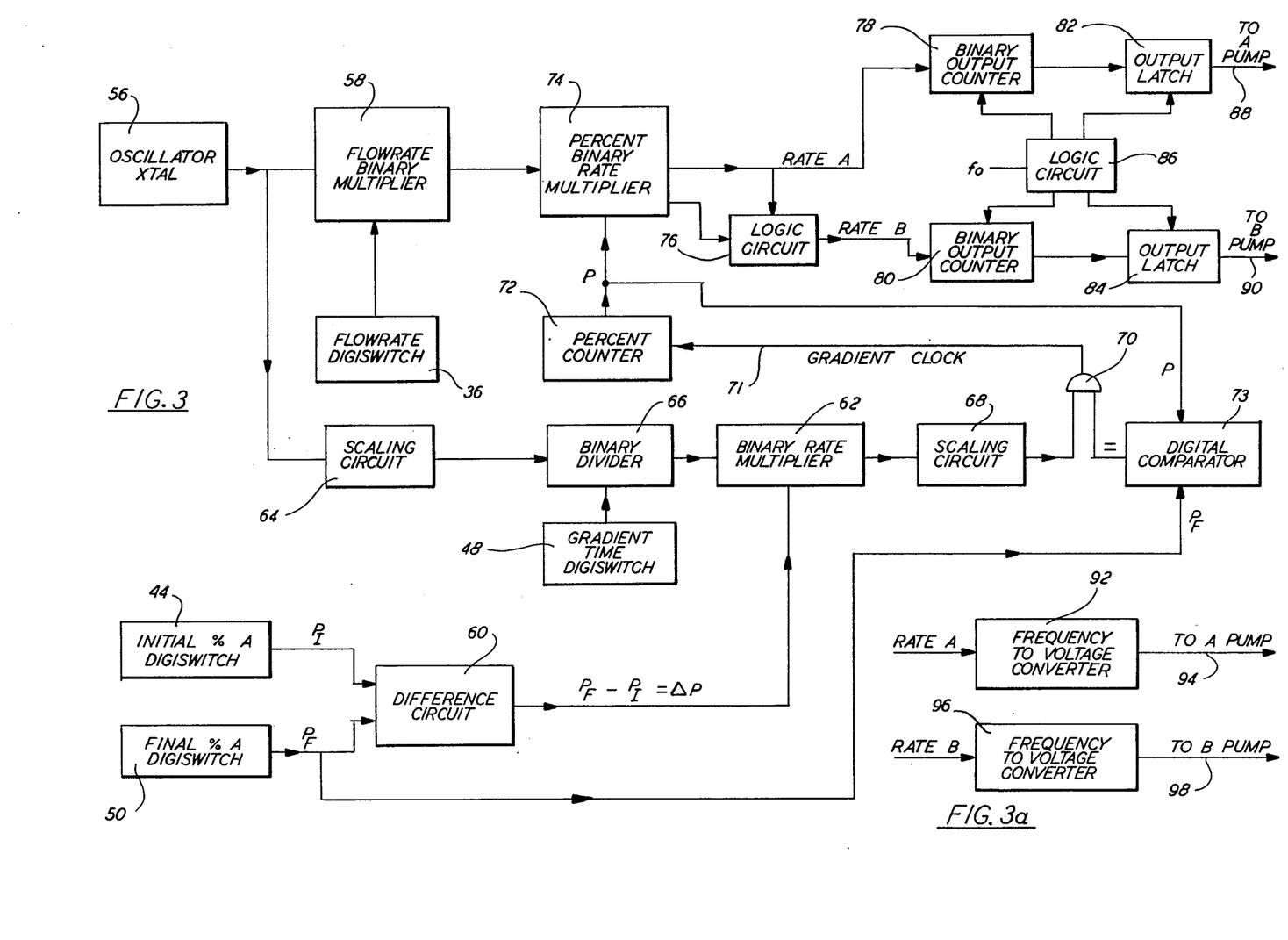
FIG. 3 is a block diagram of the circuitry of the controller of FIG. 2.
FIG. 3A is a block diagram showing an alternative form of a portion of the circuitry of FIG. 3.

Referring now to FIG. 3 there is illustrated in block diagram form the circuitry of the controller 10. A crystal oscillator 56 provides a series of clock pulses from which the flow rate frequency and the percentage update rate are derived. Specifically, the output from the oscillator is coupled to a flow rate binary multiplier 58, which also receives an input from the flow rate digiswitch 36. This switch is a two digit switch which provides a binary coded decimal number, N, representing the total flow desired, to the flow rate binary multiplier. The multiplier 58 outputs a clock frequency which equals (N/100) times the oscillator frequency on the average, where N is the flow digiswitch setting. This frequency output is proportional to the total flow rate of pumps A and B.

A difference or subtract circuit 60 receives a first input from the Initial % A digiswitch 44, which corresponds to the starting percentage for the gradient and is in the form of a binary number $P_I$. Circuit 60 receives a second input from the Final % A digiswitch 50, which corresponds to the final percentage for the gradient and is in the form of a binary number PF. The span, $P_F - P_I = \Delta P$ of the gradient is calculated by the digital subtract circuit 60 and inputted as a binary number to $\Delta P$ binary rate multiplier 62.

A scaling circuit 64 divides the master clock pulses from the oscillator 56 down to produce a properly scaled frequency, which is outputted to a binary divider 66. This binary divider divides the scaled frequency by the count set on the gradient time digiswitch 48 to produce an output frequency corresponding to the desired gradient duration. The binary rate multiplier 62 receives the output of the binary divider 66 and the output of the difference circuit 60 and multiplies them together to produce an output frequency proportional to the $\Delta P$ of the gradient. This output is scaled and smoothed in frequency by a scaling circuit 68 and after passing through AND gate 70, it serves as a gradient clock pulse input, indicated at 71 in FIG. 3, to a percent counter 72. The percent counter accumulates counts of the fixed gradient clock until the final percentage count is reached. One output of the percent counter is coupled to a digital comparator 73, which compares the actual count P on the percentage counter against the final percent $P_F$. As long as the actual percent is less than the final percent, the gradient clock is allowed to be inputted to the percent counter once the gradient has started. When the actual percent equals the final percent, the gradient clock is inhibited from the percent counter due to the AND gate 70, and the gradient is finished. The output P from the percent counter 72 is also inputted into a percent binary rate multiplier 74. Thus, the rates A and B are changed via the changing count inputted to the percent binary rate multiplier to produce a linear gradient. The percent binary multiplier outputs two clock outputs, one which equals (P/100) times its input frequency on the average indicated as rate A in FIG. 3, and the other which passes through logic circuit 76 equals 1−(P/100) times its input frequency on the average indicated as Rate B, where P is the percent counter number. That is, the output of the percent binary rate multiplier, as gated by the logic circuit 76, produces pulse rates representing % A and % B.

Still referring to FIG. 3, the output indicated as Rate A from the percent binary rate multiplier 74 is directed to a binary output counter 78, while the output indicated as Rate B is directed to a second binary output counter 80. Output latch 82 and output latch 84 are coupled to the counters 78 and 80, respectively. Logic circuit 86, which receives scaled clock pulses $f_o$ is coupled to the counters and latches. Thus, the binary counters accumulate the counts of Rate A, representing the percent of A, and of Rate B, representing the percent of B, respectively, during a period of time $\Delta T$ of the scaled clock frequency $f_o$, which are latched at the end of $\Delta T$ into the output latches. The numbers which are latched represent scaled binary numbers proportional to the desired rate of flow of the A pump and the desired rate of flow of the B pump. The output counters are then cleared and another $\Delta T$ counter period produces the next count, and so on. In effect, this circuit performs a frequency to digital number conversion. These binary numbers, as indicated at 88 and 90, are then inputted into the pumps A and B (12 and 14) of FIG. 1 to set the flow rates of said pumps.

FIG. 3A shows an alternative form of a portion of the circuitry of FIG. 3. That is, the output indicated as Rate A is inputted directly into a digital to analog converter (frequency to voltage) 92, which outputs a signal 94 to pump A to set its flow rate. In a similar manner the output indicated as Rate B is inputted directly into a second digital to analog converter (frequency to voltage) 96, which outputs a signal 98 to pump B to set its flow rate.

Figure 4:
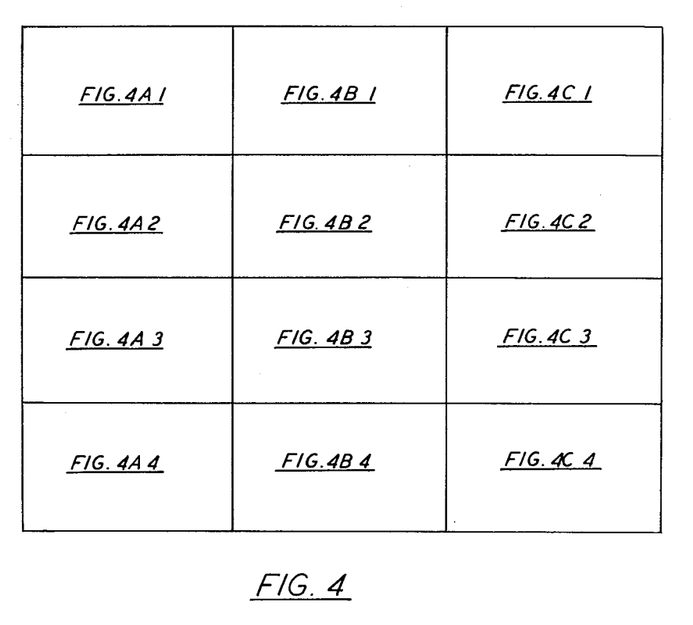
Figure 4A:
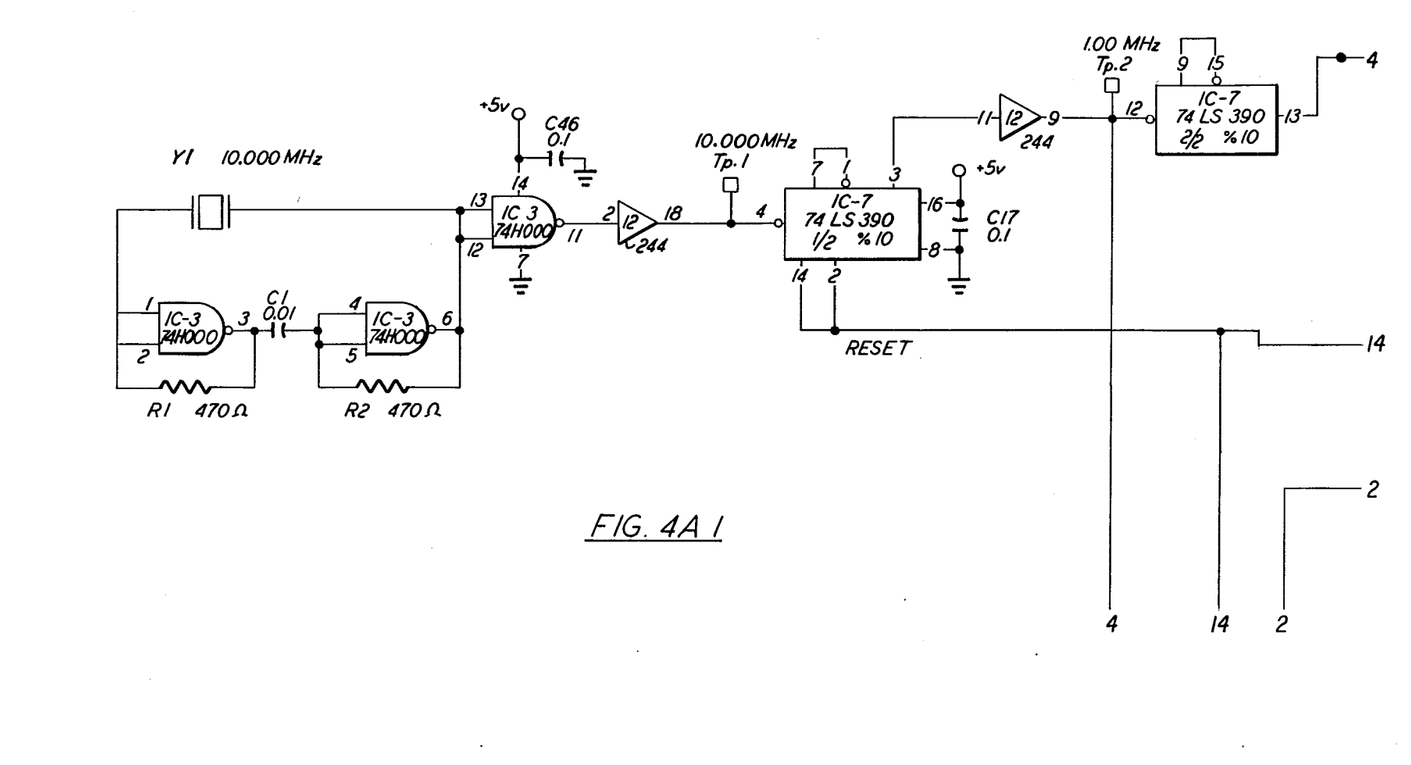
Figure 4A:
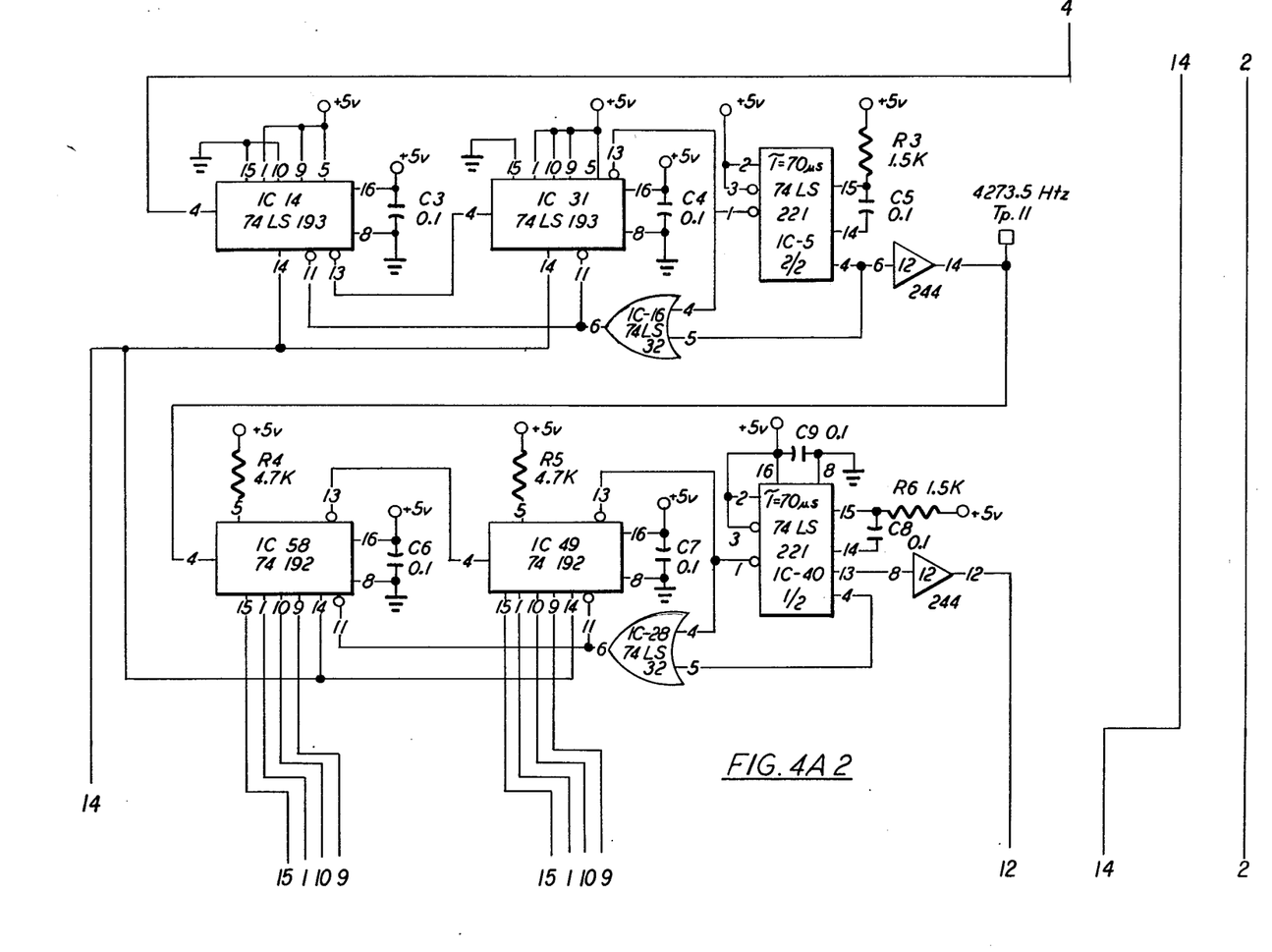
Figure 4A:
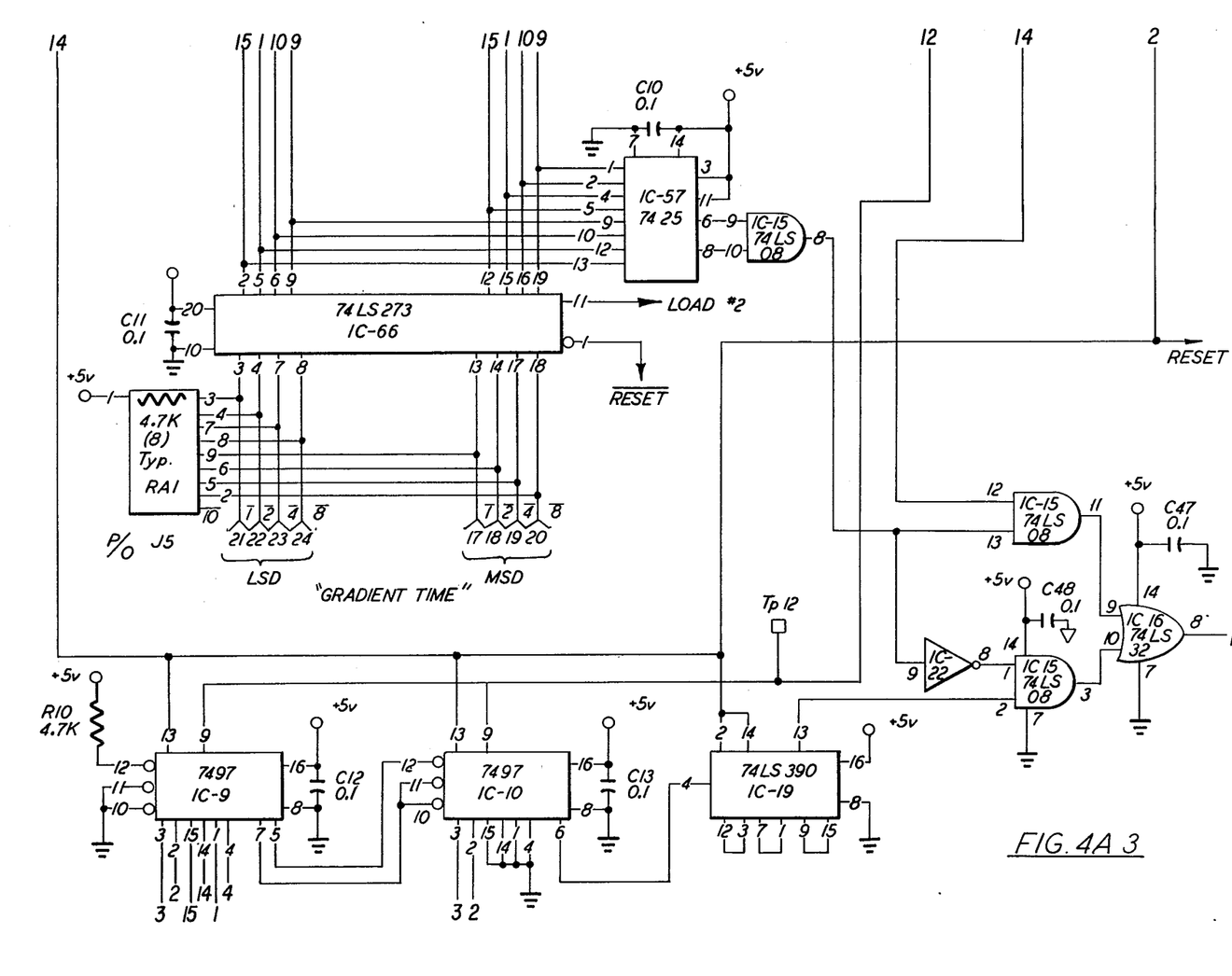
FIGS. 4A, 4B and 4C are positioned to form a circuit diagram of one actual implementation of the invention.
Figure 4A:
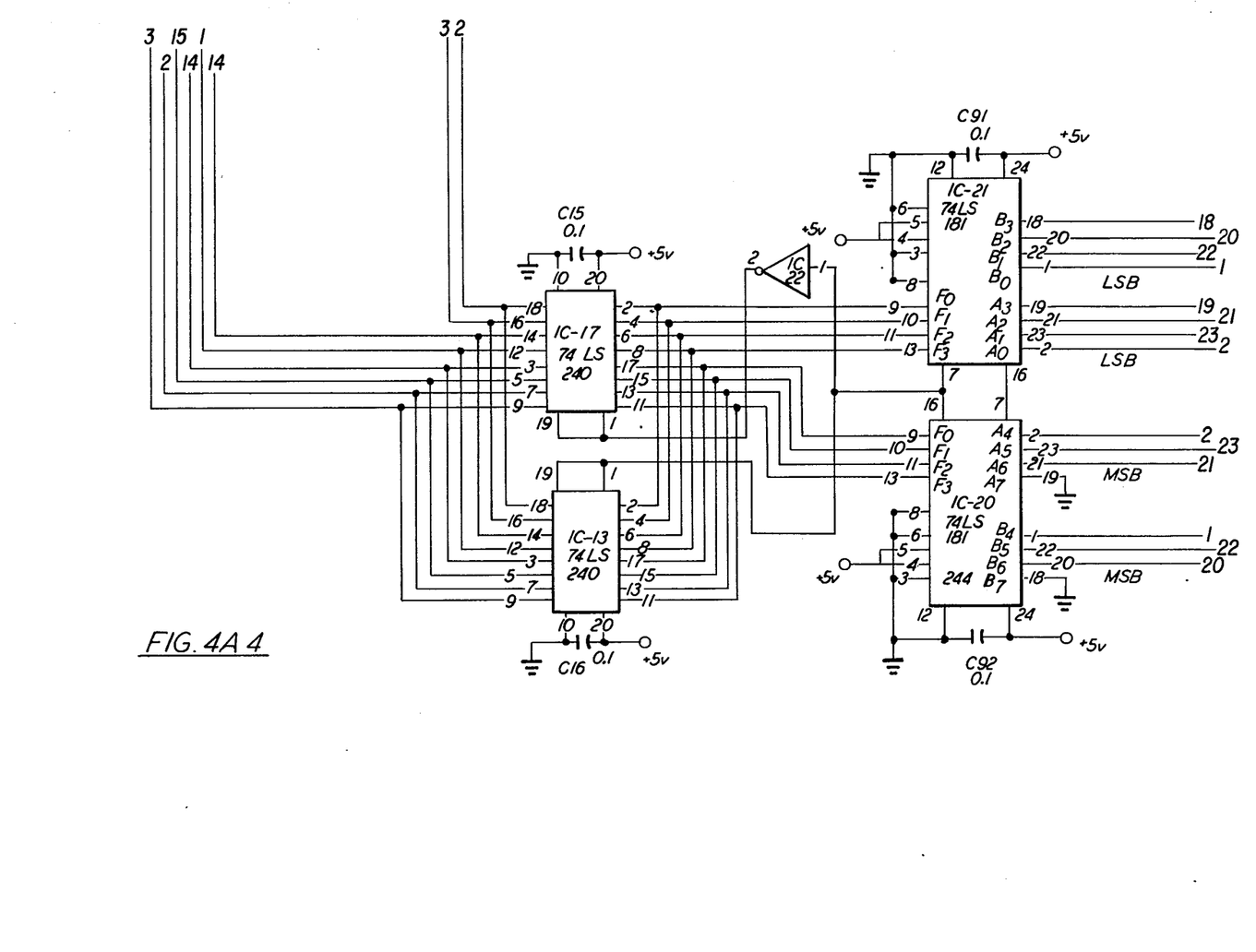
Figure 4B:
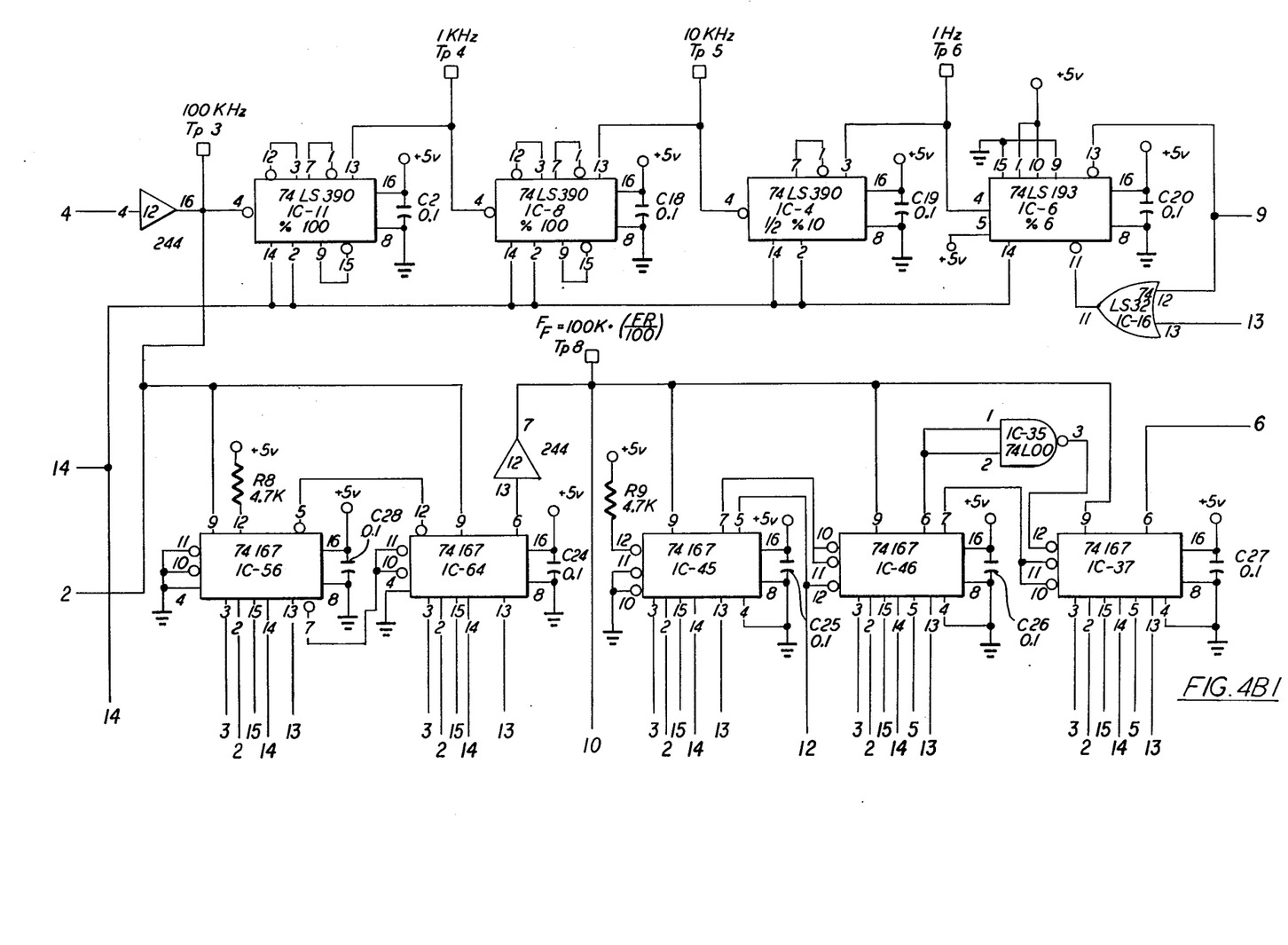
Figure 4B:
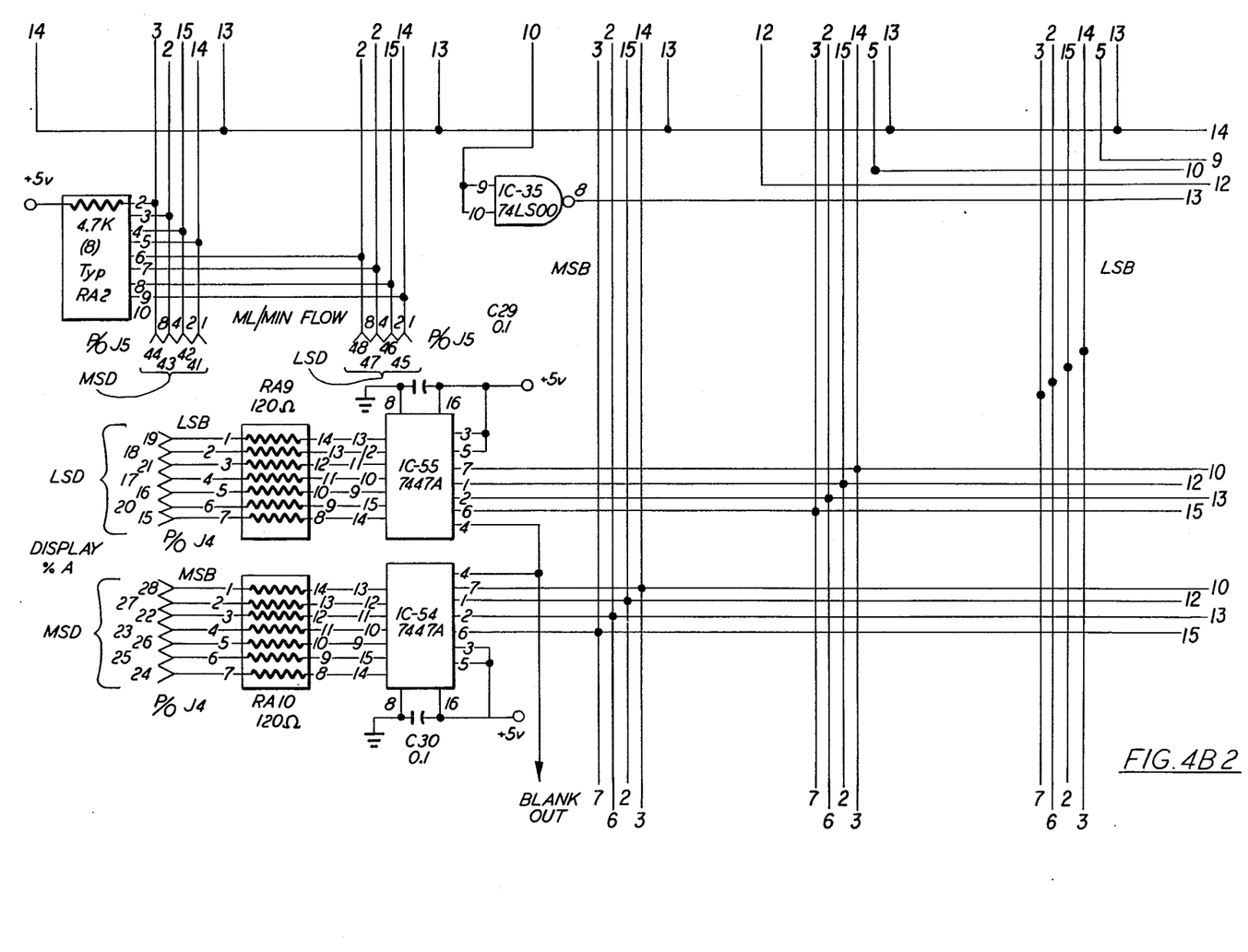
Figure 4B:
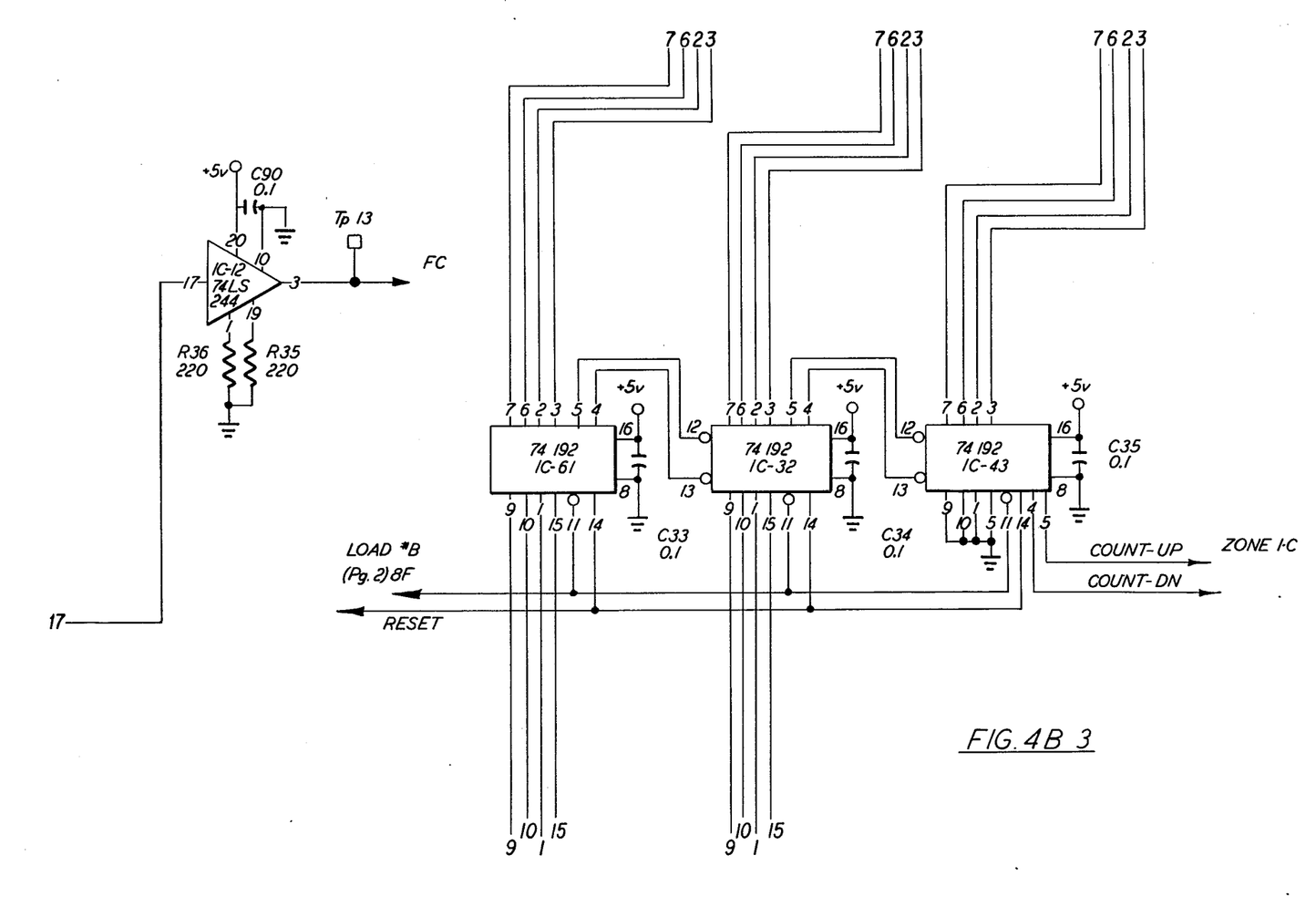
Figure 4C:
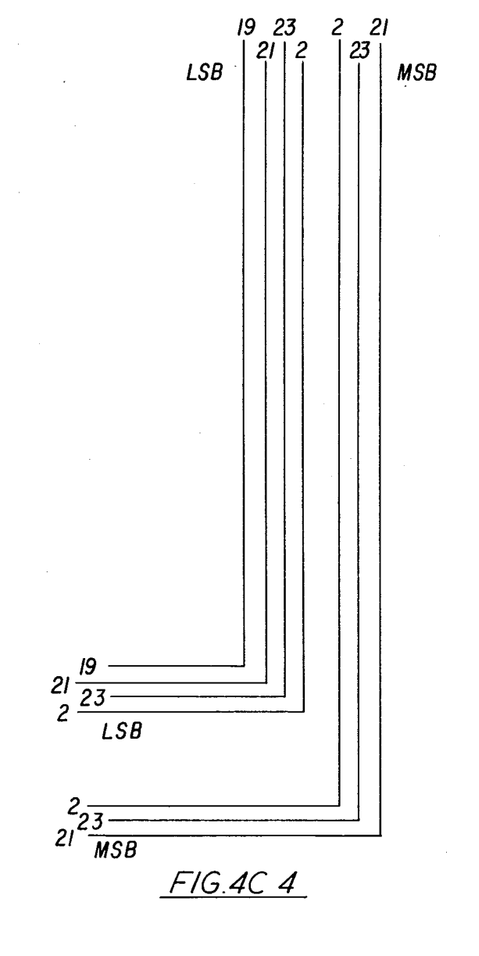
Figure 4C:
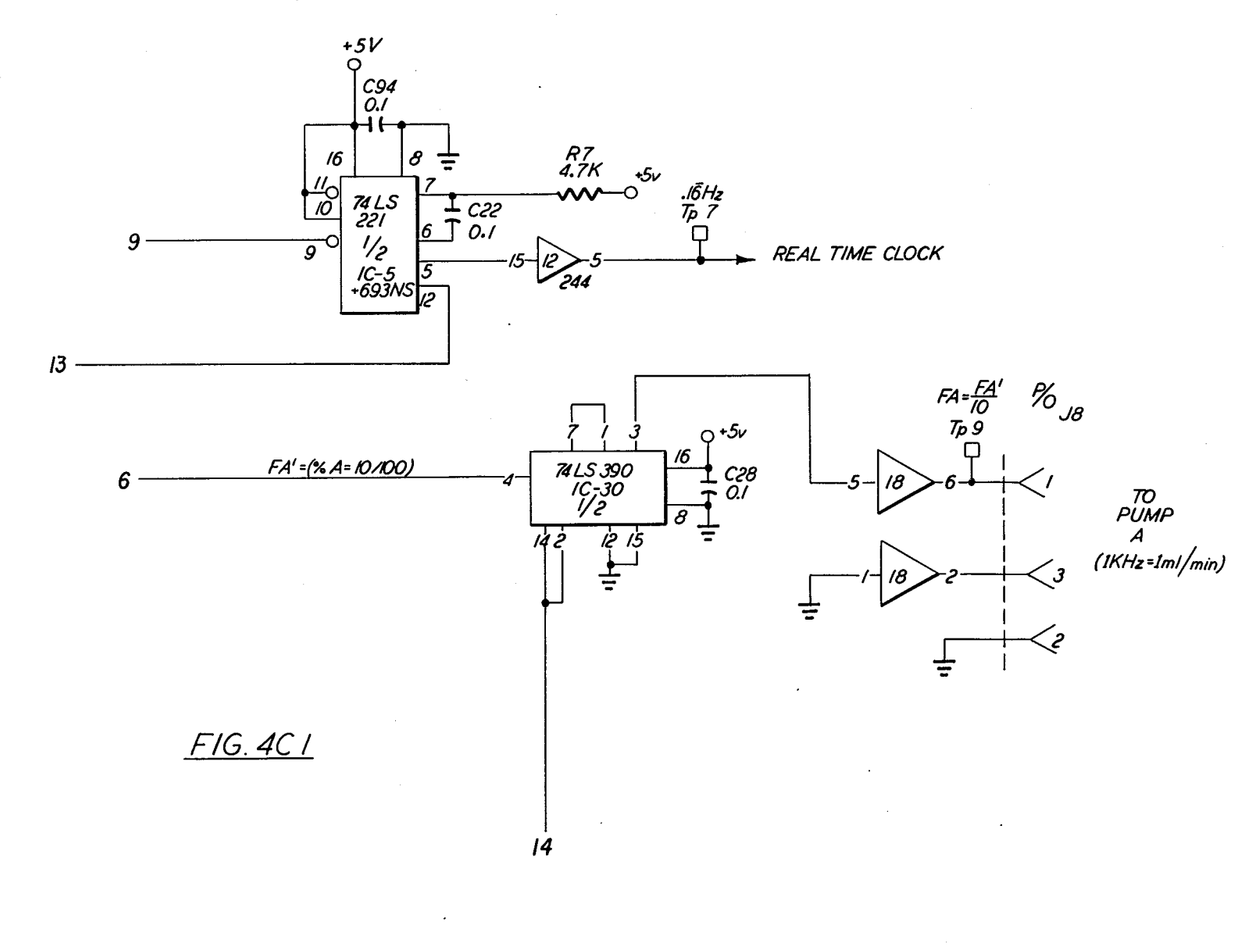
Figure 4C:
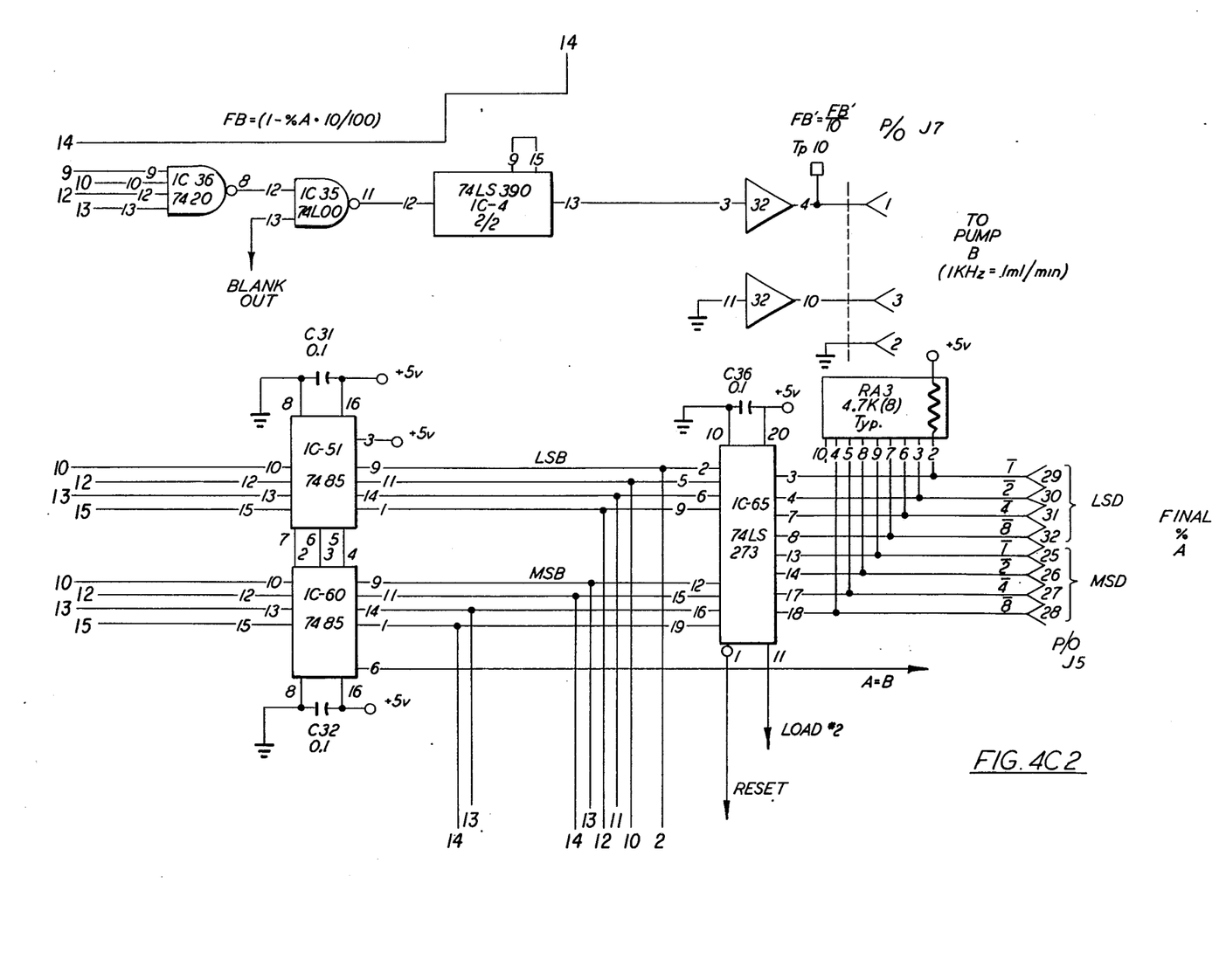
Figure 4C:
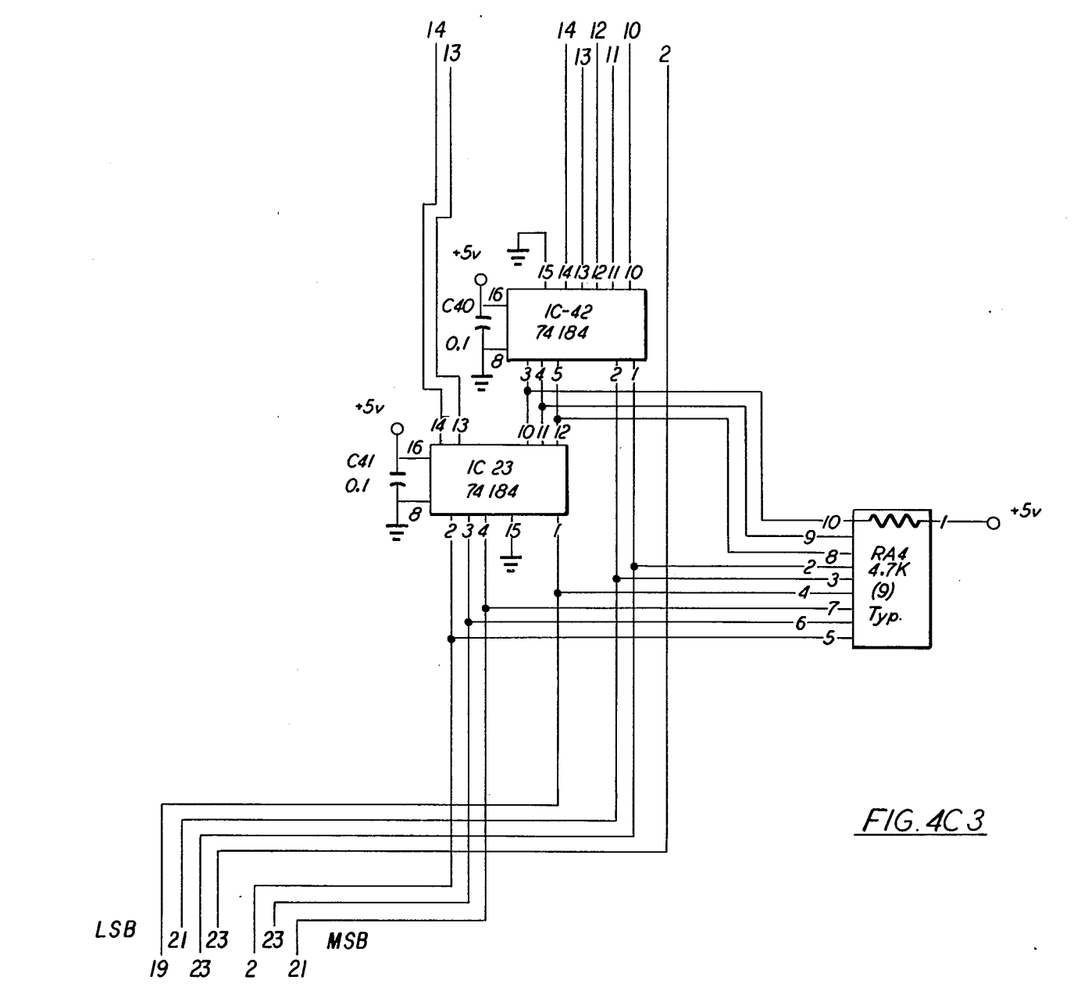

FIG. 4 is a detailed circuit diagram of one actual implementation of the new liquid chromatography pump controller of the invention. Those of skill in the art will observe throughout the drawing that circuit components have been assigned parameter values or standard commercial designations. This is done purely for clarity and reader convenience and is not intended as a limitation on component value or type nor as a restriction on the scope of the invention. Alternate circuits may be used, and the components may have to be changed to optimize the circuit for use in other applications of the invention.

It will thus be seen that the present invention does indeed provide a new and improved controller, which is superior to prior art such controllers particularly with respect to drift and reproducibility.

Although a certain particular embodiment of the invention is herein disclosed for purposes of explanation, various modifications thereof, after study of this specification, will be apparent to those skilled in the art to which the invention pertains, and reference should accordingly be had to the appended claims in determining the scope of the invention.

What is claimed is:

1. A controller for creating a linear gradient dual solvent flow pattern in a dual pump liquid chromatography system wherein one pump pumps one solvent and the other pump pumps the second solvent, said controller comprising:

first clock means for producing a timing signal;

second means for inputting a preselected first digital signal representative of an initial value for one of the two solvents;

third means for inputting a preselected second digital signal representative of a final value for said one of two solvents;

fourth means responsive to said second and third means for outputting a third digital signal representative of the difference between said initital and said final values;

fifth means manually setable for providing a fourth digital signal representative of a preselected time duration of said linear gradient;

sixth digital means for regulating said timing signal to produce a fifth digital signal proportional to said fourth digital signal;

seventh digital means, responsive to the fifth digital signal and the third digital signal, for producing a sixth digital signal representing digital counts proportional to the span of the gradient;

eighth means for accumulating digital counts from said sixth digital signal and outputting a seventh signal corresponding thereto;

said clock means producing a second timing frequency signal;

ninth means for providing an eighth digital signal representative of the total flow rate of both of said pumps;

tenth digital means, responsive to the second timing signal and the eighth digital signal for producing a ninth digital signal representative of the product of the timing frequency signal and the flow rate of both said pumps;

eleventh means for regulating said ninth digital signal responsive to said seventh signal and outputting pulse rates representing the percent rate of said first pump and the percent rate of said other pump;

twelfth means for counting said percent rates over a preselcted time interval to produce digital numbers representing the flow of the first pump and the flow of the other pump, said digital numbers being latched at the end of said preselect intervals; and thirteenth means for inputting the digital numbers latched to said pumps to set the flow rates of the pumps, respectively.

2. A controller according to claim 1 further comprising digital comparator means for comparing said seventh signal and said second signal and when said seventh signal equal said second signal inhibiting said sixth digital signal.

3. A controller according to claim 1 wherein said second means and said third means comprise digiswitches, respectively.

4. A controller according to claim 1 wherein said fifth means comprises a digiswitch.

5. A controller according to claim 1 wherein said sixth means comprises a binary divider.

6. A controller according to claim 1 wherein said seventh digital means comprises a binary rate multiplier.

7. A controller according to claim 1 wherein said eighth means comprises a percent counter.

8. A controller according to claim 1 wherein said ninth means comprises a digiswitch.

9. A controller according to claim 1 wherein said tenth digital means comprises a flow rate binary multiplier.

10. A controller according to claim 1 wherein said eleventh means comprises a percent binary rate multiplier.

11. A controller according to claim 1 wherein said twelfth means comprises a pair of binary output counters and a pair of corresponding output latches.

* * * * *